United States Patent
Burkholz et al.

(10) Patent No.: US 10,507,281 B2
(45) Date of Patent: Dec. 17, 2019

(54) CANNULA CAPTURE MECHANISM

(71) Applicant: Becton, Dickinson and Company, Franklin Lakes, NJ (US)

(72) Inventors: Jonathan Karl Burkholz, Salt Lake City, UT (US); Siddarth K. Shevgoor, Laguna Beach, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 117 days.

(21) Appl. No.: 15/461,365

(22) Filed: Mar. 16, 2017

(65) Prior Publication Data

US 2017/0274183 A1 Sep. 28, 2017

Related U.S. Application Data (60) Provisional application No. 62/314,262, filed on Mar. 28, 2016.

(51) Int. Cl.
  *A61M 5/158* (2006.01)
  *A61M 25/06* (2006.01)
  *A61M 5/32* (2006.01)

(52) U.S. Cl.
  CPC ............ *A61M 5/158* (2013.01); *A61M 5/322* (2013.01); *A61M 25/0618* (2013.01)

(58) Field of Classification Search
  CPC .......... A61M 25/0618; A61M 25/0631; A61M 25/0612
  See application file for complete search history.

(56) References Cited

U.S. PATENT DOCUMENTS

| | | | |
|---|---|---|---|
| 5,486,164 A | 1/1996 | Streck | |
| 6,443,929 B1* | 9/2002 | Kuracina | A61B 5/15003 604/192 |
| 8,257,322 B2 | 9/2012 | Koehler et al. | |
| 8,496,623 B2 | 7/2013 | Burkholz | |
| 2013/0023835 A1 | 1/2013 | Kuracina et al. | |
| 2014/0039399 A1 | 2/2014 | Burkholz | |
| 2015/0202412 A1* | 7/2015 | Nakajima | A61M 25/0631 604/263 |

FOREIGN PATENT DOCUMENTS

| | | | | |
|---|---|---|---|---|
| WO | WO 2014/054166 | * | 4/2014 | ........ A61M 25/0631 |
| WO | 2015/082559 | | 6/2015 | |

* cited by examiner

*Primary Examiner* — Emily L Schmidt
(74) *Attorney, Agent, or Firm* — Kirton & McConkie; Craig Metcalf; Kevin Stinger (57) ABSTRACT

A cannula capture mechanism is described herein. The capture mechanism may include an inner housing, outer housing, and a cannula. The outer housing may be configured to move between a compressed and a decompressed state. An outer surface of the inner housing may include one or more interlock components. When the cannula is exposed from a distal end of the inner housing, the one or more interlock components may interact with one or more interlock surfaces formed in another surface of the catheter device. When the cannula is retracted proximally within the inner housing, the inner housing may contract radially inward causing the one or more interlock components to be separated from the one or more interlock surfaces and the outer housing to move to the decompressed state and extend distally over a distal portion of the inner housing.

19 Claims, 8 Drawing Sheets

CANNULA CAPTURE MECHANISM

RELATED APPLICATIONS

This application claims the benefit of U.S. Provisional Patent Application No. 62/314,262, filed on Mar. 28, 2016, and entitled CANNULA CAPTURE MECHANISM, which is incorporated herein in its entirety.

BACKGROUND OF THE INVENTION

This disclosure relates generally to vascular access devices and associated methods. More specifically, this disclosure discusses a cannula capture mechanism that is configured to capture a cannula tip in a manner that locks the cannula in a shielded position. The cannula capture mechanism can be used with catheter assemblies.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly to help guide the needle and to facilitate its cooperation with the catheter. At least the inner surface of the distal portion of the catheter tightly engages the outer surface of the needle to prevent peelback of the catheter and, thereby, facilitate insertion of the catheter into the blood vessel. The catheter and the introducer needle are often assembled so that the distal tip of the introducer needle extends beyond the distal tip of the catheter. Moreover, the catheter and needle are often assembled so that, during insertion, the bevel of the needle faces up, away from the patient's skin. The catheter and introducer needle are generally inserted at a shallow angle through the patient's skin into a blood vessel.

In order to verify proper placement of the needle and/or catheter in the blood vessel, the operator generally confirms that there is "flashback" of blood into a flashback chamber associated with the needle assembly. Flashback generally entails the appearance of a small amount of blood, which is visible within the needle assembly or between the needle and the catheter. Once proper placement of the distal tip of the catheter into the blood vessel is confirmed, the operator may apply pressure to the blood vessel by pressing down on the patient's skin over the blood vessel, distal to the introducer needle and the catheter. This finger pressure momentarily occludes the vessel, minimizing further blood flow through the introducer needle and the catheter.

The operator may then withdraw the introducer needle from the catheter. The needle may be withdrawn into a needle tip cover or needle cover that extends over the needle's tip and prevents accidental needle sticks. In general, a needle tip cover includes a casing, sleeve, or other similar device that is designed to trap/capture the needle tip when the introducer needle is withdrawn from the catheter and the patient. After the needle is withdrawn, the catheter is left in place to provide intravenous access to the patient.

The separation of the introducer needle assembly from the catheter portions of the catheter assembly presents numerous potential hazards to the operators and others in the area. As indicated above, there is a risk of accidental needle sticks if the needle tip is not secured properly in a needle tip shield. Additionally, because the needle has been in contact with blood in the patient's vasculature, blood is often present on the needle's exterior as well as inside the lumen of the needle. As the needle is withdrawn from the catheter, there is a risk that this blood will drip from the needle tip or come into contact with other surfaces to expose people and equipment to blood. Additionally, it has been observed that withdrawing a needle from a catheter assembly often imparts energy to the parts of the needle assembly. For instance, during needle withdrawal, bending forces can be applied (either unintentionally or intentionally) to the needle. Such energy has been observed to cause blood to splatter or spray from the needle when the needle vibrates and shakes as it becomes free from the catheter assembly and releases the stored energy.

The present disclosure discusses a cannula capture mechanism that allows a needle to be retracted from an unshielded position to a shielded position in which the cannula feature is trapped. Accordingly, the described capture mechanism is configured to lock the needle in the shielded position to significantly limit or prevent accidental sticks and blood exposure after the needle is withdrawn from a catheter assembly.

BRIEF SUMMARY OF THE INVENTION

The present application relates to a cannula capture mechanism. In some embodiments, the capture mechanism may include a cannula, an inner housing, and an outer housing. In some embodiments, the inner housing may include multiple arms, which may extend distally from a proximal end of the inner housing. In some embodiments, when the cannula is exposed from a distal end of the inner housing, the multiple arms of the inner housing may be splayed radially outward. In some embodiments, when the cannula is retracted proximally within the inner housing, the outer housing may be configured to move from a compressed state to an decompressed state ("decompressed state" as used herein may refer to a state in which the outer housing is less compressed than when the outer housing is in the compressed state and does not necessarily refer to a state without any compression of the outer housing). In some embodiments, when the outer housing is in the decompressed state, the outer housing may bias the arms of the inner housing together, which may securely close the distal end of the inner housing and prevent the cannula from exiting the distal end of the inner housing.

In some embodiments, when the cannula is retracted proximally within the inner housing, the cannula may be prevented from exiting the distal end of the inner housing as well as a proximal end of the inner housing. Thus, the cannula may be bi-directionally trapped within the inner housing when the cannula is retracted proximally within the inner housing. For example, in some embodiments, the cannula may include a cannula feature. In some embodiments, when the cannula is retracted proximally within the inner housing, the cannula feature may be configured to contact the proximal end of the inner housing to prevent the cannula from exiting the proximal end of the inner housing.

In some embodiments, a compressible portion of the outer housing may be compressed when the outer housing is in the compressed state and decompressed when the outer housing is in the decompressed state. In some embodiments, the compressible portion may include a spring, an elastomer, or another compressible member. In some embodiments, the compressible portion may be baffled or accordion-shaped. In some embodiments, the compressible portion may be compressible along an axis aligned with a longitudinal axis of the cannula.

In some embodiments, movement of the outer housing to the decompressed state may cause a distal end of the outer housing, which may be radially rigid and/or coupled with the compressible portion, to slide distally over a distal portion of the inner housing, which may bias the arms of the inner housing together and seal or close the distal end of the inner housing. The distal portion of the inner housing may include at least a portion of the arms and may have a first outer diameter when the cannula is exposed from the distal end of the inner housing and a second outer diameter when the cannula is retracted proximally within the inner housing. In some embodiments, the second outer diameter may be approximately equal to an inner diameter of the distal end of the outer housing and may be smaller than the first outer diameter.

In some embodiments, the cannula capture mechanism may be secured to one or more of the following when the cannula is exposed from the distal end of the inner housing: a catheter adapter, a side port of the catheter adapter, a non-luer accessible port of the catheter adapter, a septum activator, and a septum. In some embodiments, an inner surface of the catheter adapter may be configured to secure the inner housing within the catheter adapter when the cannula is exposed from the distal end of the inner housing. In some embodiments, the inner surface of the catheter adapter may also be configured to separate from the inner housing to release the inner housing from the catheter adapter when the cannula is retracted proximally within the inner housing.

In further detail, an outer surface of the inner housing may include one or more interlock components that may interact with one or more interlock surfaces formed in the inner surface of the catheter adapter. In some embodiments, contraction of the inner housing radially inward, in response to retraction of the cannula proximally within the inner housing, may cause the one or more interlock components to be separated from the one or more interlock surfaces, which may allow removal of the cannula capture mechanism from the catheter adapter, a distal tip of the cannula being shielded inside the inner housing.

In some embodiments, an inner surface of the side port, the septum activator, and/or the septum may be similarly configured to secure the cannula capture mechanism within the catheter adapter when the cannula is exposed from the distal end of the inner housing and/or to separate from the inner housing when the cannula is retracted proximally within the inner housing. For example, the one or more interlock components of the outer surface of the inner housing may interact with one or more interlock surfaces formed in the inner surface of the side port, the septum activator, and/or the septum. Contraction of the inner housing radially inward, in response to retraction of the cannula proximally within the inner housing, may cause the one or more interlock components to be separated from the one or more interlock surfaces of the side port, the septum activator, and/or the septum, which may allow removal of the cannula capture mechanism from the catheter adapter, a distal tip of the cannula being shielded inside the inner housing. In some embodiments, the septum may be configured to move distally over a fixed septum activator, and the outer surface of the inner housing may interact with one or more interlock surfaces formed in the inner surface of the septum.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the bi-directional cannula feature capture mechanism, as represented in FIGS. 1 through 7, is not intended to limit the scope of the invention, as claimed, but is merely representative of some presently preferred embodiments of the invention.

Generally, this application relates to a cannula capture mechanism. In other words, this application discusses a cannula capture mechanism that allows a cannula to be moved from an unshielded position to a shielded position in which the cannula is prevented from moving distally out of the capture mechanism. In some embodiments, the cannula is bi-directionally trapped and also prevented from moving proximally out of the capture mechanism. As used herein, the term "unshielded" may refer to circumstances in which the cannula's distal tip is exposed from the inner housing of the capture mechanism. Conversely, the term "shielded" may refer to circumstances in which the cannula's tip is covered, shielded, or otherwise protected by the inner housing of the capture mechanism. In some embodiments, because the capture mechanism allows the cannula to be locked in the shielded position, the capture mechanism may prevent unintended sticking and/or blood exposure. To better explain the capture mechanism, a more detailed description of the mechanism is given below, followed by a more detailed description of the mechanism's use.

Figure 1:
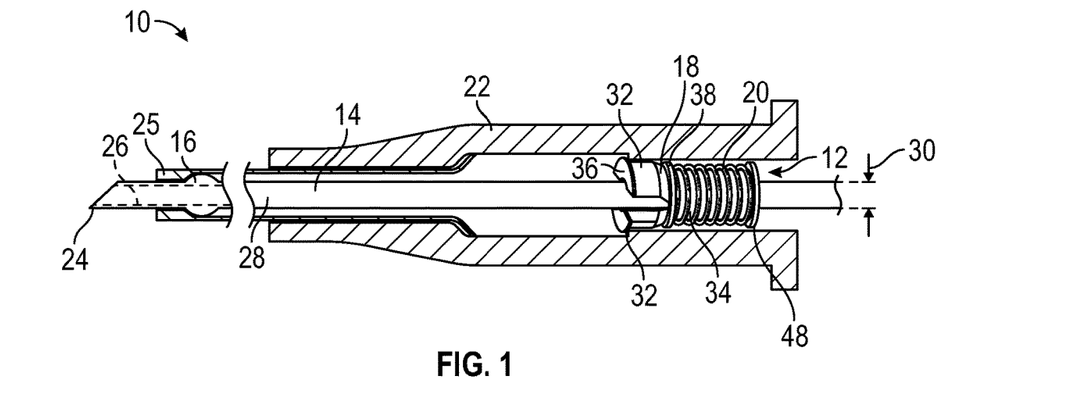
FIG. 1 illustrates a partial cut-away view of a representative embodiment of a catheter device that includes a cannula capture mechanism in which a cannula is exposed from the catheter device.

FIG. 1 illustrates a representative embodiment of a catheter device 10 that includes a cannula capture mechanism 12. As illustrated in FIG. 1, in some embodiments, the cannula capture mechanism 12 may include a cannula (e.g., needle 14), an engageable cannula feature (e.g., needle feature 16), an inner housing 18, and an outer housing 20. Additionally, FIG. 1 illustrates that the capture mechanism 12 may be selectively be coupled with a catheter adapter 22. To provide a better understanding of the capture mechanism 12, each of the aforementioned components is described in below in further detail.

FIG. 1 illustrates the capture mechanism 12 may include a cannula (e.g., needle 14). As used herein, the terms "cannula" and "cannulae" may refer to virtually any rigid tube that is configured to be inserted into an animal's body to draw off or to introduce fluid, wherein the tube includes a sharpened tip that allows the tube to puncture the body and access an intended space. Some examples of such cannulae may include hypodermic needles and other cannulae that may expose their operator to the risk of unintended sticking or blood exposure.

The cannula may include any cannula that can be used with the described capture mechanism, including, but not limited to, a hypodermic needle. Where the cannula includes a hypodermic needle, the cannula may include any suitable type of hypodermic needle, including an introducer needle for use in an IV catheter assembly (e.g., an over-the-needle peripheral IV catheter assembly).

As illustrated in FIG. 1, the cannula may include an introducer needle 14. When the needle 14 is exposed from the inner housing 18 in the unshielded position, the needle 14 may extend axially through the inner housing 18 and the outer housing 20 so that the distal tip 24 extends past the distal end 36 of the inner housing 18 and the distal end 38 of the outer housing 20. Additionally, in the unshielded position, a distal portion of the needle 14 optionally extends into a catheter 25 and the outer housing 20 is optionally coupled to the catheter adapter 22.

In some embodiments, the needle 14 may include any component or characteristic that prevents the distal tip 24 of the needle 14 from exiting the proximal end of the inner housing 18. For instance, the needle 14 may include any suitable needle feature that has an OD that is greater than an OD of the needle 14 or has at least one surface that extends laterally past the OD of the needle 14. In one example, the needle 14 includes an engageable needle feature 16, such as a notched crimp feature, a welded ferrule feature, a notch feature, a crimp feature, or another cannula feature that has an outer diameter ("OD") that extends laterally past an OD of the cannula. In this example, the needle feature 16 may include a proximal engagement that is adapted to contact a surface of the inner housing 18 to restrict proximal movement of the needle feature 16 in the inner housing 18. In some embodiments, the needle feature 16 may include one or more one-way barbs or a notch. Regardless of the specific type of needle feature 16, the needle feature 16 may have any suitable characteristic. For instance, the needle feature 16 may be any suitable shape or size.

In some embodiments, the needle 14 may have any characteristic that is suitable for use with an IV catheter assembly. By way of illustration, FIG. 1 shows an embodiment in which the needle 14 includes a sharpened distal tip 24, a lumen 26 (not directly illustrated), an elongated tubular portion 28 with a substantially constant OD 30, and an engageable needle feature 16. Additionally, each of the needle's aforementioned components may include any suitable characteristic. For example, the distal tip 24 of the needle 14 may include a standard bevel, a short bevel, a true short bevel, a bias grind point, a vet point, a lancet point, a deflected point (anti-coring), or another suitable needle point. In another example, the lumen 26 and elongated tubular portion 28 may be any suitable size. For instance, the needle 14 may be any length or gauge (e.g., from a 7 to a 33 on the Stubs scale) that allows it to be used as the needle 14 in an IV assembly.

As previously mentioned, the capture mechanism 12 may also include the inner housing 18. In some embodiments, the inner housing 18 may be split longitudinally to form multiple arms 32. The inner housing 18 may include any number of arms, such as, for example, two, three (as illustrated in FIG. 1), or four. In some embodiments, the arms 32 may extend distally from a proximal portion, such as a proximal end, of the inner housing 18. In some embodiments, when the needle 14 is exposed from the distal end 36 of the inner housing 18, the needle 14 may be configured to bias the arms 32 apart. For example, in some embodiments, when the needle 14 is exposed from the distal end 36 of the inner housing 18 in the unshielded position, the arms 32 of the inner housing 18 may be resiliently splayed radially outward by the needle 14, as illustrated in FIG. 1.

The inner housing 18 may be constructed of any suitable material or materials, such as, for example, a metal, a metal alloy, a ceramic, a plastic, a polymer, etc. Advantageously, a rigid plastic may allow the distal tip 24 to embed in an inner surface of the inner housing 18 when in the shielded position. Surfaces of the inner housing 18 that contact the needle 14 may include a coating to lower friction between the surfaces and the needle 14 and/or improve a feel of the needle 14 sliding relative to the surfaces. The coating may include, for example, a lubricant and/or a conformal coating. In some embodiments, the inner housing 18 may be a single piece. In some embodiments, the inner housing 18 may include multiple pieces that may be coupled together in any number of ways, such as, for example, threading, fitting, snapping, connecting, attaching, fastening, clipping, hooking, or any other suitable means of coupling.

The capture mechanism may also include the outer housing 20. In some embodiments, when the needle 14 is retracted proximally within the inner housing 18 to the shielded position, the outer housing 20 may be configured to move from a compressed state, illustrated in FIGS. 1 and 2A, to a decompressed state illustrated in FIG. 2B. In some embodiments, when the outer housing 20 is in the decompressed state, the outer housing 20 may bias the arms 32 of the inner housing 18 together, which may securely seal or close the distal end 36 of the inner housing 18 and prevent the needle 14 from exiting the distal end 36 of the inner housing 18.

Figure 2A:
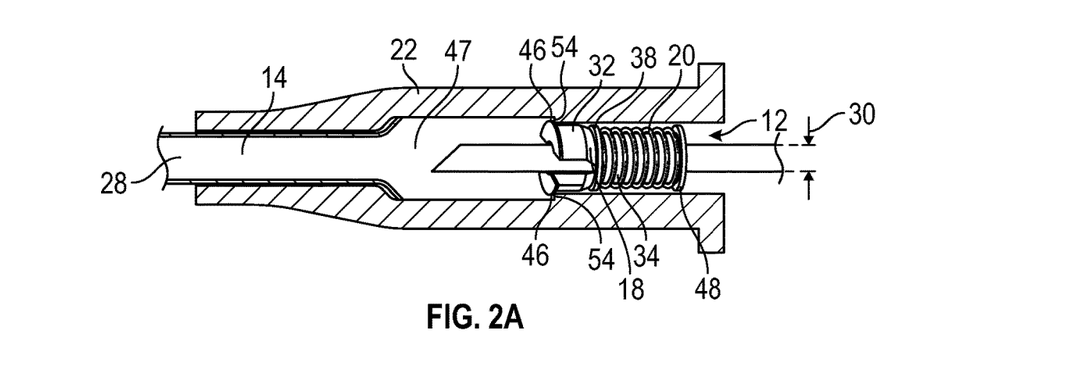
FIG. 2A illustrates a partial cut-away view of a representative embodiment of the cannula capture mechanism of FIG. 1 in which the cannula is exposed from a distal end of an inner housing.
Figure 2B:
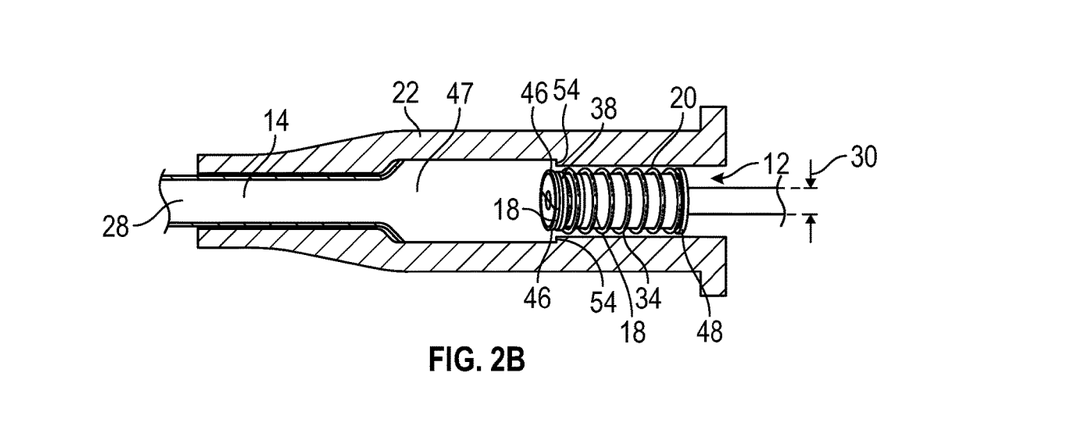
FIG. 2B illustrates a partial cut-away view of a representative embodiment of the cannula capture mechanism of FIG. 1 in which the cannula is retracted within the inner housing.

The outer housing 20 may axially slide or expand over at least a portion of the inner housing 18 when the outer housing 20 decompresses or moves from the compressed state, illustrated in FIG. 2A, to the decompressed state, illustrated in FIG. 2B. The portion of the inner housing 18 over which the outer housing 20 slides or expands may be any suitable size or have any suitable shape. For instance, the portion of the inner housing 18 may be substantially cylindrical, cuboidal, tubular, etc. A restoring force in the distal direction may cause the outer housing 20 to axially slide or expand when the outer housing 20 moves from the compressed state to the decompressed state.

In some embodiments, the outer housing 20 may include a compressible portion 34, which may be disposed between and/or coupled with a distal end 38 of the outer housing 20 and a proximal end 48 of the outer housing 20. In some embodiments, the compressible portion 34 of the outer housing 20 may be compressed when the outer housing 20 is in the compressed state and decompressed when the outer housing 20 is in the decompressed state. In some embodiments, the compressible portion 34 may be compressible along an axis aligned with the needle 14. In some embodiments, the compressible portion 34 may include a spring, an elastomer, or another compressible member. In some embodiments, the compressible portion 34 may be cylindrical. In some embodiments, the spring may be cylindrical and/or coiled. In some embodiments, the compressible portion 34 may be baffled or accordion-shaped. In these and other embodiments, the compressible portion 34 may include a tube or sleeve, which may be constructed of an elastomer, silicone, a liquid silicone rubber material, or another suitable material. In some embodiments, the compressible portion 34 may enclose the inner housing 18, which may act as a redundant mechanism to ensure any residual blood on the needle 14 stays within the cannula capture mechanism 12.

In some embodiments, an inner surface of the outer housing 20 may include a coating to lower friction between the inner surface and the inner housing 18 and/or an outer surface of the outer housing 20 may include the coating. The coating may include, for example, a lubricant and/or a conformal coating.

In some embodiments, a proximal end 48 of the outer housing 20 may be directly coupled with the proximal end of the inner housing 18, and the distal end 38 of the outer housing 20 may move distally away from the proximal end of the outer housing 20 and the proximal end of the inner housing 18 when the outer housing 20 moves to the decompressed state. In some embodiments, movement of the outer housing 20 to the decompressed state may cause the distal end 38 of the outer housing 20, which may be radially rigid and/or coupled with the compressible portion 34, to slide or move distally along the inner housing 18.

As illustrated in FIG. 2A, in some embodiments, an inner surface of the catheter adapter 22 may be configured to secure the inner housing 18 within the catheter adapter 22 when the needle 14 is exposed from the inner housing 18. In some embodiments, the inner surface of the catheter adapter 22 may be configured to separate from the inner housing 18 to release the inner housing 18 from the catheter adapter 22 when the needle 14 is retracted proximally within the inner housing 18, as illustrated in FIG. 2B. In further detail, an outer surface of the inner housing may include one or more interlock components 46 that may interact with one or more interlock surfaces 54 formed in the inner surface of the catheter adapter 22. The interlock components 46 may be biased against a corresponding interlock surface 54 of the catheter adapter 22 when the needle 14 is exposed from the distal end 36 of the inner housing 18 in the unshielded position. Contraction of the inner housing 18 radially inward, in response to retraction of the needle 14 proximally within the inner housing 18, may cause the one or more interlock components 46 to be separated from the one or more interlock surfaces 54, which may allow removal of the cannula capture mechanism 12 from the catheter adapter 22, the distal tip 24 of the needle 14 being shielded inside inner housing 18. Accordingly, unintentional needle sticks may be prevented, and the cannula capture mechanism 12 may be safely disposed.

Where the cannula capture mechanism 12 is used in conjunction with the catheter adapter 22, the two can be coupled in any suitable manner that allows the cannula capture mechanism 12 to be coupled to the adapter 22 when the needle 14 is in the unshielded position and to be uncoupled from the adapter 22 when the needle 14 is in the shielded position. Also, the capture mechanism 12 may be used with any suitable catheter adapter 22. Further, where the inner housing 18 is selectively coupled within the catheter adapter 22 by a coupling mechanism, the coupling mechanism may be located in any suitable position. For example, the interlock components 46 and the interlock surfaces 54 may be disposed proximally or distally within a lumen 47 of the catheter adapter 22.

Figure 3A:
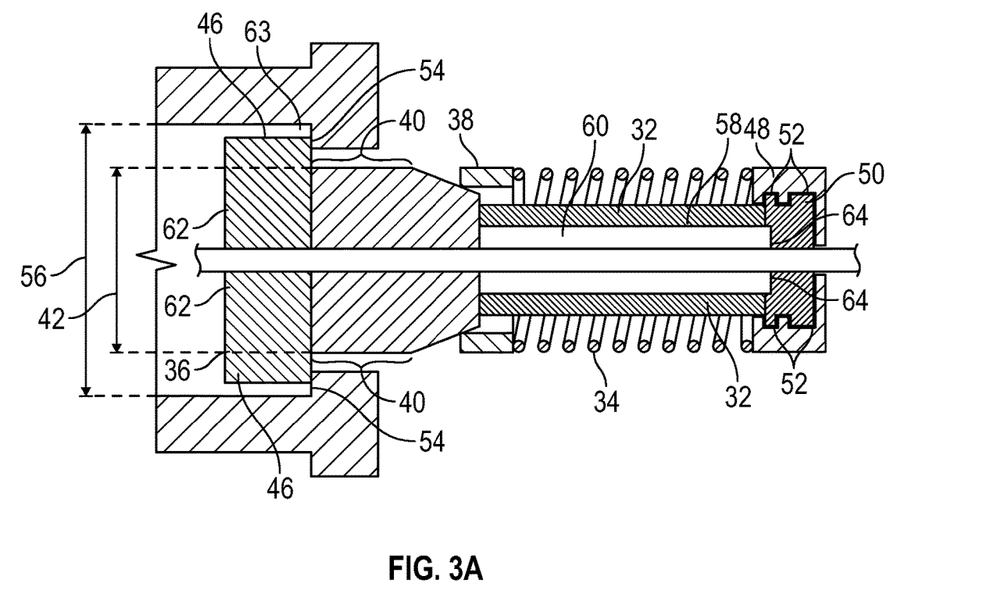
FIG. 3A illustrates a cross sectional view of a representative embodiment of the cannula capture mechanism of FIG. 1 in which the cannula is exposed from the distal end of the inner housing.
Figure 3B:
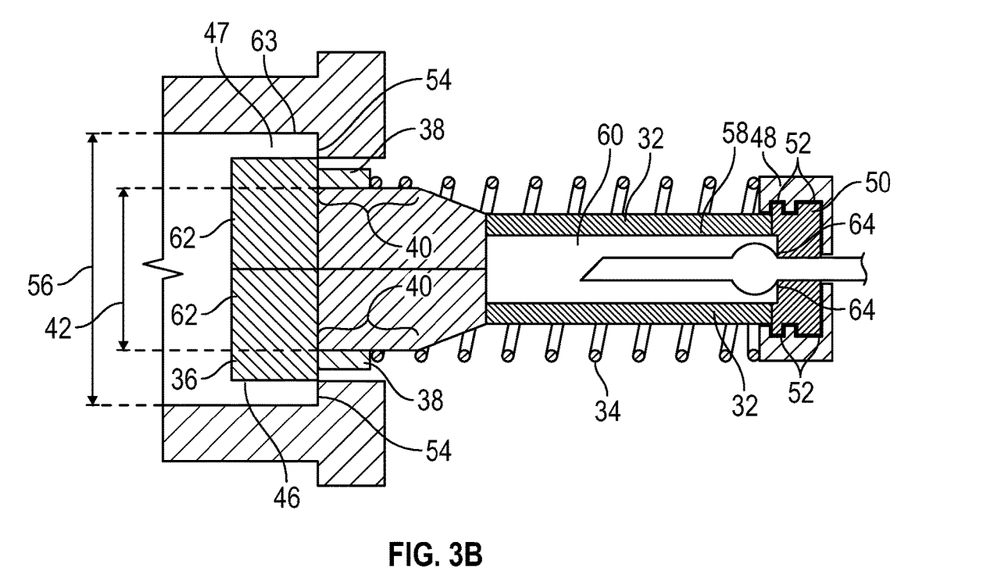
FIG. 3B illustrates a cross sectional view of a representative embodiment of the cannula capture mechanism of FIG. 1 in which the cannula is retracted within the inner housing.

FIGS. 3A-3B illustrate cross sectional views of the cannula capture mechanism 12. As illustrated in FIG. 3B, in some embodiments, the distal end 38 may slide over and snugly fit around a distal portion 40 of the inner housing 18, which may bias the arms 32 of the inner housing 18 together and securely close the distal end 36 of the inner housing 18. The distal portion 40 of the inner housing 18 may include at least a portion of the arms 32 and may have a first outer diameter 42 when the needle 14 is exposed from the distal end 36 of the inner housing 18 and the outer housing 20 is in the compressed state, as illustrated in FIG. 3A. The distal portion 40 of the inner housing 18 may have a second outer diameter 44 when the needle 14 is retracted proximally within the inner housing 18 and the outer housing 20 is in the decompressed state, illustrated in FIG. 3B. In some embodiments, the second outer diameter 44 may be approximately equal to an inner diameter of the distal end 38 of the outer housing 20 and may be smaller than the first outer diameter 42.

In some embodiments, the distal end 38 may be configured to stop at the distal portion 40 due to a length of the compressible portion 34 and/or a presence of the interlock components 46 of the inner housing 18, which may be disposed at least proximate the distal end 36 of the inner housing 18 and may act as a stop. In some embodiments, an inner diameter 56 of the inner housing 18 at the interlock components 46 may be larger than the first outer diameter 42 and the second outer diameter 44.

As illustrated in FIGS. 3A-3B, the proximal end 48 of the outer housing 20 may be directly coupled with the proximal end 50 of the inner housing 18. The proximal end 48 may be directly coupled with the proximal end 50 in any number of ways, such as, for example, threading (e.g., threads 52), fitting, snapping, connecting, attaching, fastening, clipping, hooking, or any other suitable means of coupling.

In some embodiments, the inner housing 18 may include inner walls 58, which may define an interior space 60 through which the needle 14 axially extends. As illustrated in FIG. 3B, in some embodiments, when the needle 14 is retracted proximally within the inner housing 18 to the shielded position, the needle 14 may be prevented from exiting the distal end 36 of the inner housing 18. For example, the distal tip 24 may contact a surface of the inner housing 18 to restrict distal movement of the needle 14. In further detail, distal ends of the arms 32 may include transverse barriers 62 that extend inwardly and are configured to extend towards the longitudinal axis of the needle 14. The transverse barriers 62 may contact the distal tip 24 to restrict distal movement of the needle 14 when the needle 14 is proximally retracted within the inner housing 18. In some embodiments, the transverse barriers 62 may contact and/or overlap with each other when the needle 14 is proximally retracted within the inner housing 18 and may form a seal that may prevent blood and/or the distal tip 24 from exiting the distal end 36 of the inner housing 18. The transverse barriers 62 may thereby provide a needle tip capture mechanism that encloses the distal tip 24 to protect people from unintentional sticking and/or to reduce the risk of blood exposure. Additionally or alternatively, the arms 32 of the inner housing may include another suitable type of needle shielding component.

As illustrated in FIG. 3B, in some embodiments, when the needle 14 is retracted proximally within the inner housing 18, the needle 14 may also be prevented from exiting the proximal end 50 of the inner housing 18. In some embodiments, the needle feature 16 may be retracted proximally until it contacts the proximal end 50 of the inner housing 18, preventing the distal tip 24 from exiting the proximal end 50 of the inner housing 18. For instance, the proximal end 50 of the inner housing 18 may include any suitable type of needle shielding component. By way of example, as illustrated in FIGS. 3A-3B, the proximal end 50 may include transverse barriers 64 that extend inwardly and are configured to extend towards the longitudinal axis of the needle 14. The transverse barriers 64 may contact the needle feature 16 to restrict proximal movement of the needle 14 when the needle 14 is proximally retracted within the inner housing 18. As another example, the proximal end 50 may include a washer, cylinder, wedge, or other suitable component that includes a hole that allows the needle 14 to pass but does not allow the needle feature 16 to pass.

As mentioned, in some embodiments, the distal end 38 of the outer housing 20 may be radially rigid. In some embodiments, the distal end 38 of the outer housing 20 may be substantially radially rigid such that the distal end 38 has a degree of flexibility. In these embodiments, an internally applied radial force may cause the distal end to flex. The distal end 38 may radially rigid due to any number of factors. For example, the distal end 38 may include an end portion of a spring, which may be constructed of a metallic or polymeric or other suitable material. As another example, in some embodiments, the distal end 38 may be coupled with a radially rigid component. In some embodiments, the radially rigid component may be sized and configured to fit around the distal end 38. In some embodiments, in order to provide stability, the radially rigid component may be sized and configured to fit into the lumen 47 of the catheter adapter 22 and abut inner walls 63 of the catheter adapter 22 or to fit into a lumen or interior space of a septum activator and abut inner walls of the septum activator. In some embodiments, the radially rigid component may include a ring constructed of a metallic or polymeric or other suitable material. In some embodiments, the radially rigid component may be separate or integrally formed with the outer housing 20.

Figure 4A:
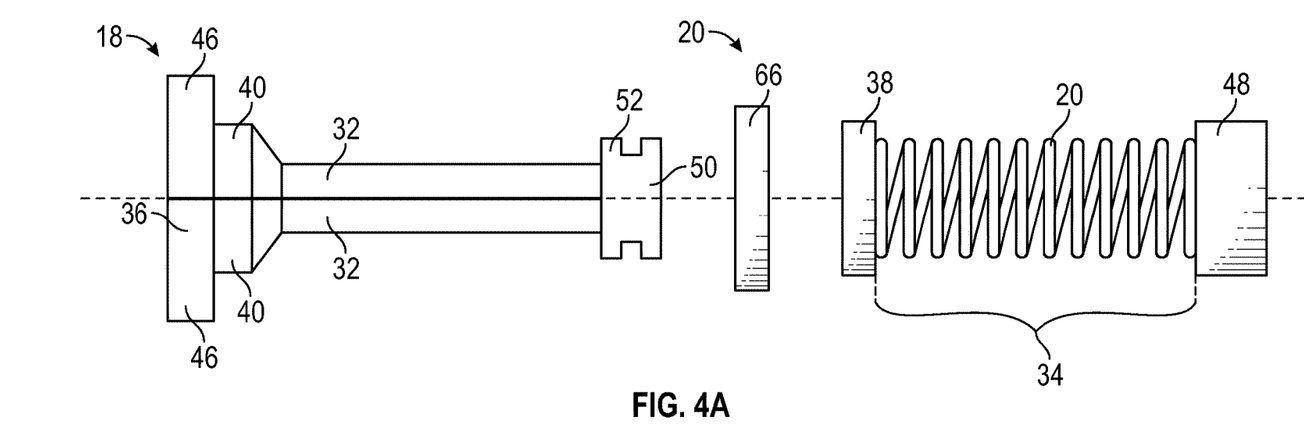
FIG. 4A illustrates an exploded view of a representative embodiment of an outer housing and an inner housing of the cannula capture mechanism of FIG. 1.
Figure 4B:
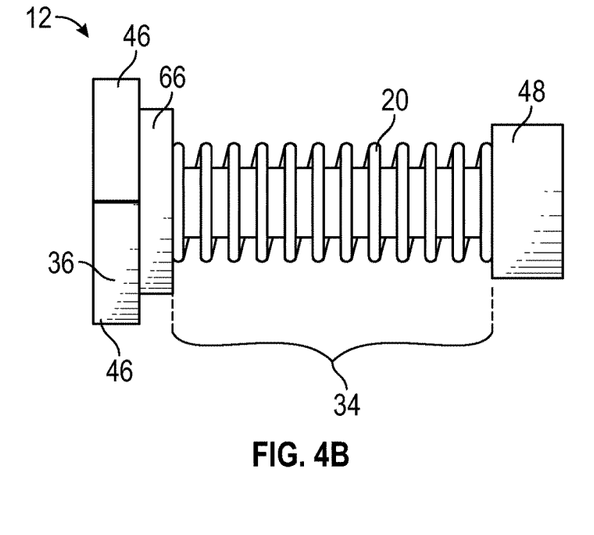
FIG. 4B illustrates the outer housing and the inner housing of the cannula capture mechanism of FIG. 1 coupled together.

FIG. 4A illustrates an exploded view of a representative embodiment of the outer housing 20 and the inner housing 18 in which a radially rigid component 66 is separate from the outer housing 20. Alternatively, in some embodiments, the outer housing 20 may include the radially rigid component 66. For example, the radially rigid component 66 may be coupled with the distal end 38 of the outer housing 20. As another example, the radially rigid component 66 may include an end of the spring portion, which may be coiled. The radially rigid component 66 may increase the rigidity of the distal end 38.

Figure 5A:
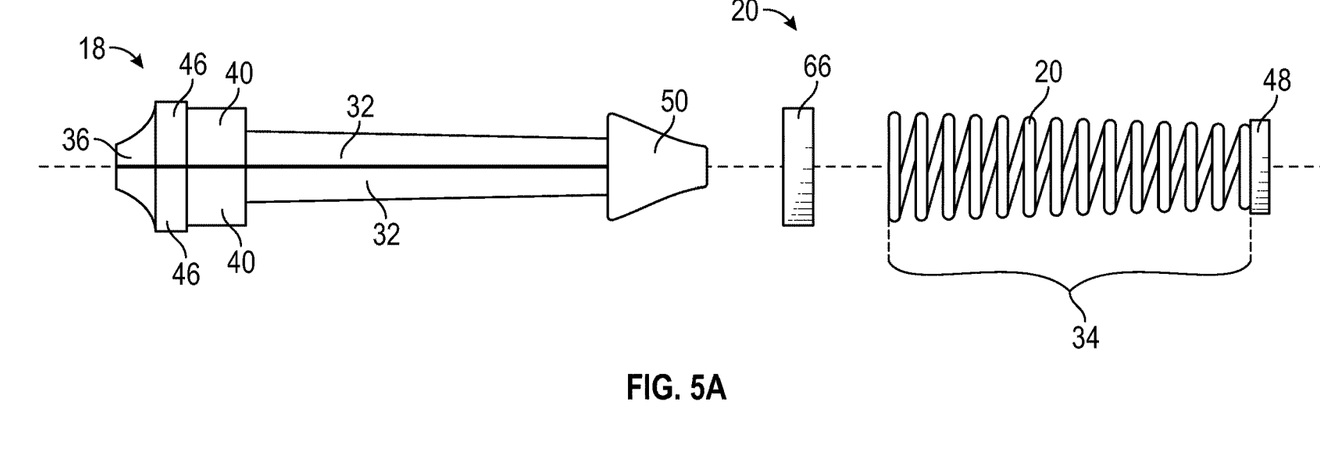
FIG. 5A illustrates an exploded view of a representative embodiment of an outer housing and an inner housing of another cannula capture mechanism.
Figure 5B:
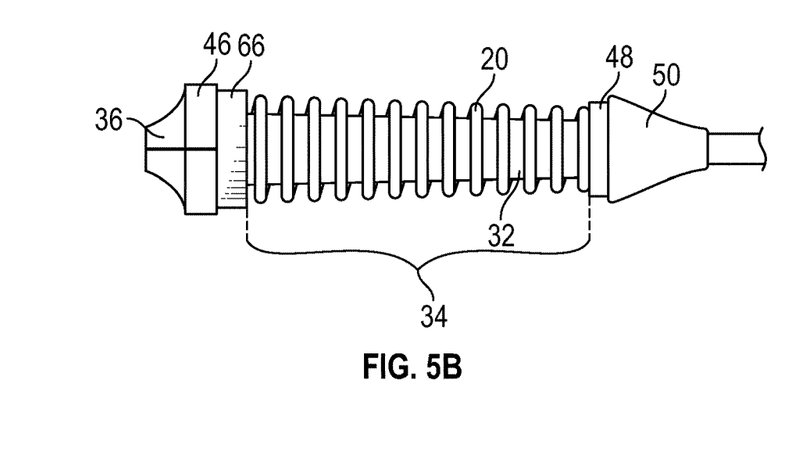
FIG. 5B illustrates the outer housing and the inner housing of the cannula capture mechanism of FIG. 5A coupled together.

FIG. 5A illustrates an exploded view of a representative embodiment of an outer housing 20 and an inner housing 18 of another cannula capture mechanism 12. In some embodiments, the cannula capture mechanism 12 may correspond to the cannula capture mechanism 12 of FIGS. 1-4. In some embodiments, the radially rigid component 66 may be integrally formed with the distal end 38 of the outer housing 20. Also, as illustrated in FIGS. 5A-5B, in some embodiments, as opposed to directly coupling the proximal end 48 of the outer housing 20 to the proximal end 50 of the inner housing 18 via threads 52 (illustrated, for example, in FIGS. 3A-3B and 4A), the proximal end 50 of the inner housing 18 may have a larger outer diameter than an inner diameter of the proximal end 48 of the outer housing 20 and may act as a stop, preventing the outer housing 20 from moving in a proximal direction.

Figure 6A:
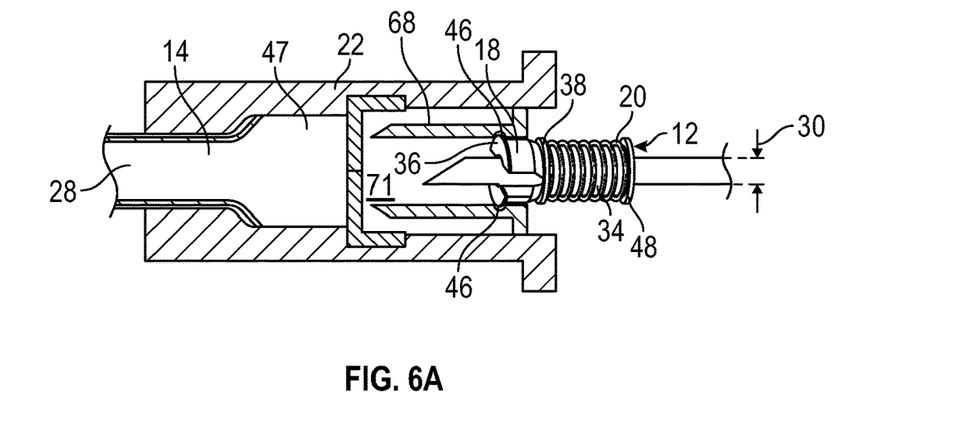
FIG. 6A illustrates a partial cut-away view of a representative embodiment of the cannula capture mechanism of FIG. 1 in which the cannula is exposed from the inner housing, and the cannula capture mechanism is secured to a septum activator.
Figure 6B:
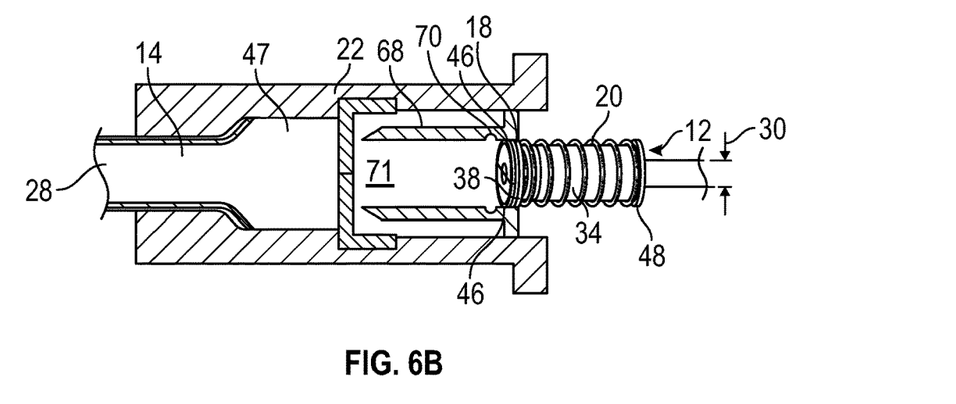
FIG. 6B illustrates a partial cut-away view of a representative embodiment of the cannula capture mechanism of FIG. 1 in which the cannula is retracted within the inner housing, and the cannula capture mechanism is separated from the septum activator.

The inner housing 18 can be configured to selectively and removably couple to any suitable catheter adapter 22 or another component of the catheter device 10, in any suitable manner. For example, as illustrated in FIG. 6A, an inner surface of a septum activator 68 may be configured to secure the inner housing 18 within the catheter adapter 22 when the needle 14 is exposed from the distal end 36 of the inner housing 18 and/or to separate from the inner housing 18 when the needle 14 is retracted proximally within the inner housing 18. For example, the one or more interlock components 46 of the outer surface of the inner housing 18 may interact with one or more interlock surfaces 70 formed in the inner surface of the septum activator 68. In some embodiments, the interlock surfaces 70 may correspond to the interlock surfaces 54 of FIGS. 1-3. In some embodiments, a shape of the interlock surfaces 70 may prevent the inner housing 18 of the cannula capture mechanism 12 from moving proximally or distally when the needle 14 is exposed from the distal end 36 of the inner housing 18, as illustrated in FIGS. 6A-6B. Contraction of the inner housing 18 radially inward, in response to retraction of the needle 14 proximally within the inner housing 18, may cause the one or more interlock components 46 to be separated from the one or more interlock surfaces 70 of the septum activator 68, which may allow removal of the cannula capture mechanism 12 from the catheter adapter 22, the distal tip of the needle 14 being shielded inside the inner housing 18.

In some embodiments, where the cannula capture mechanism 12 is used in conjunction with the septum activator 68, the two may be coupled in any suitable manner that allows the cannula capture mechanism 12 to be coupled to the septum activator 68 when the needle 14 is in the unshielded position and to be uncoupled from the septum activator 68 when the needle 14 is in the shielded position. Also, the capture mechanism 12 may be used with any suitable septum activator 68. Further, where the inner housing 18 is selectively coupled within the septum activator 68 by a coupling mechanism, the coupling mechanism may be located in any suitable position. For example, the interlock components 46 and the interlock surfaces 70 may be disposed proximally or distally within a lumen 71 of the septum activator 68.

Figure 7A:
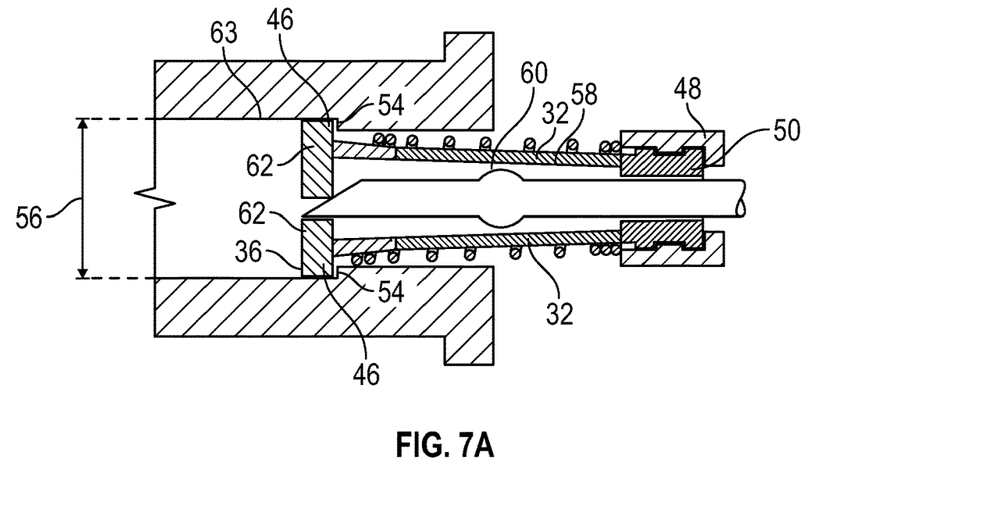
FIG. 7A illustrates a cross sectional view of a representative embodiment of the cannula capture mechanism of FIG. 1 in which a distal tip is partially exposed from the inner housing.

In some instances, slow retraction of the needle 14 proximally into the inner housing 18 may cause the transverse barriers 62 of the arms 32 to get stuck on a bevel of the needle 14, as illustrated in FIG. 7A. In these instances, the interlock components 46 may release or separate from the interlock surfaces 54 or the interlock surfaces 70 when the needle 14 is retracted proximally, but the arms 32 may not contract radially inward with enough force to cause the transverse barriers 62 to meet and shield the needle 14 within the inner housing 18.

Figure 7B:
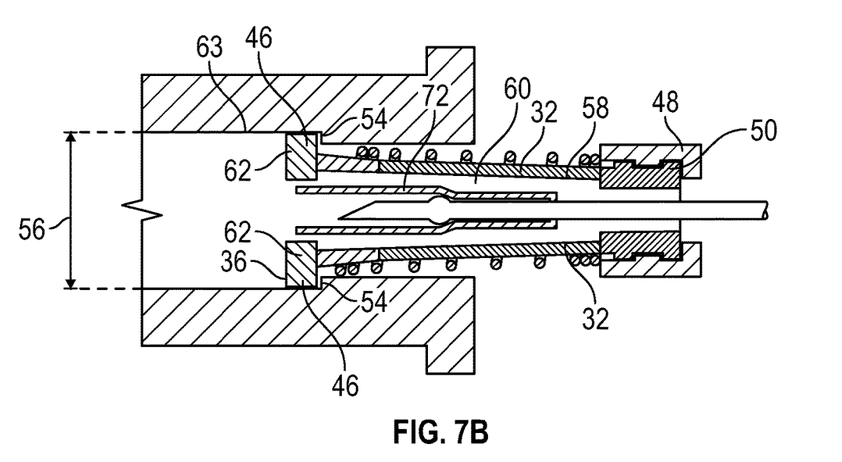
FIG. 7B illustrates a cross sectional view of a representative embodiment of the cannula capture mechanism of FIG. 1 in which the distal tip is disposed in a square-edged sleeve.

Thus, in some embodiments, the distal tip 24 may be disposed in a generally cylindrical and/or square-edged sleeve 72, as illustrated in FIG. 7B. In some embodiments, the sleeve 72 may be tubular and/or include an open distal end. Thus, when the interlock components 46 are released or separated from the interlock surfaces 54 or the interlock surfaces 70, the arms 32 may contract radially inward more suddenly, which may allow the transverse barriers 62 to meet and shield the needle 14 within the inner housing.

Figure 7C:
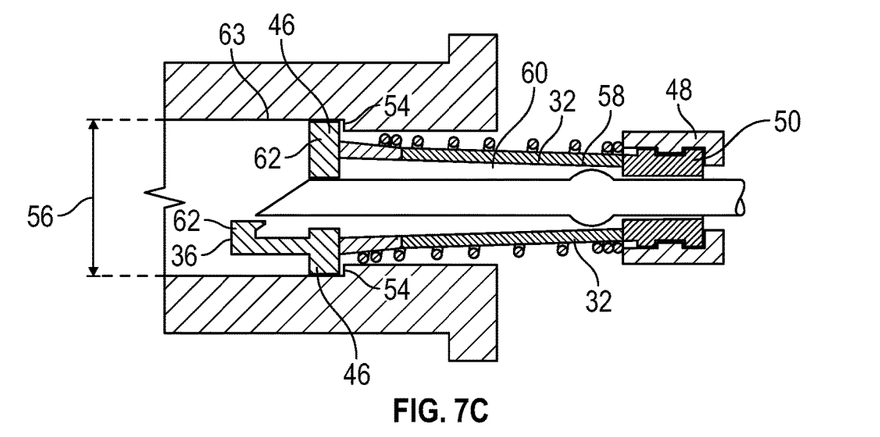
FIG. 7C illustrates a cross sectional view of a representative embodiment of another cannula capture mechanism in which a first arm and a second arm of the inner housing are different lengths.

Additionally or alternatively, lengths of the arms 32 may be different such that an inner surface 74 of a particular transverse barrier 62 is separated from an inner surface 76 of another particular transverse barrier 62 by a first length 78, as illustrated in FIG. 7C. The bevel may be a second length 80. In some embodiments, the first length may be greater than the second length in order to ensure that when the interlock components 46 are released or separated from the interlock surfaces 54 or the interlock surfaces 70, the transverse barriers 62 will prevent the needle 14 from exiting the distal end of the inner housing 18.

Figure 8:
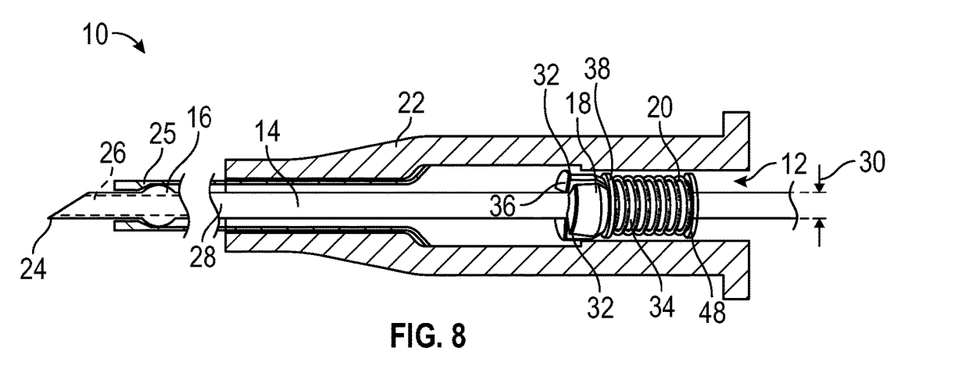
FIG. 8 illustrates a partial cut-away view of a representative embodiment of a catheter device that includes another cannula capture mechanism.

FIG. 8 illustrates a partial cut-away plan view of a representative embodiment of a catheter device 10 that includes another cannula capture mechanism 12. In some embodiments, the inner housing 18 may include three or more arms 32, as illustrated in FIG. 8.

In addition to the previously described embodiments of the cannula capture mechanism 12, the capture mechanism 12 may be modified in any suitable manner that allows it to fulfill its intended purpose. Further, the cannula capture mechanism 12 can be used in any suitable manner. By way of non-limiting illustration, FIG. 1 illustrates that before the needle 14 is inserted into a patient's blood vessel (not shown), the needle 14 extends axially through the inner 18 and outer housing 20 and through a distal tip of the catheter adapter 22. Additionally, FIG. 1 illustrates that before the needle 14 is inserted into the blood vessel, the needle feature 16 may be is disposed distal to the distal end 36 of the inner housing 18. Moreover, FIG. 1 illustrates at least a portion of the inner housing 18 may be disposed within the outer housing 20.

Figure 9:
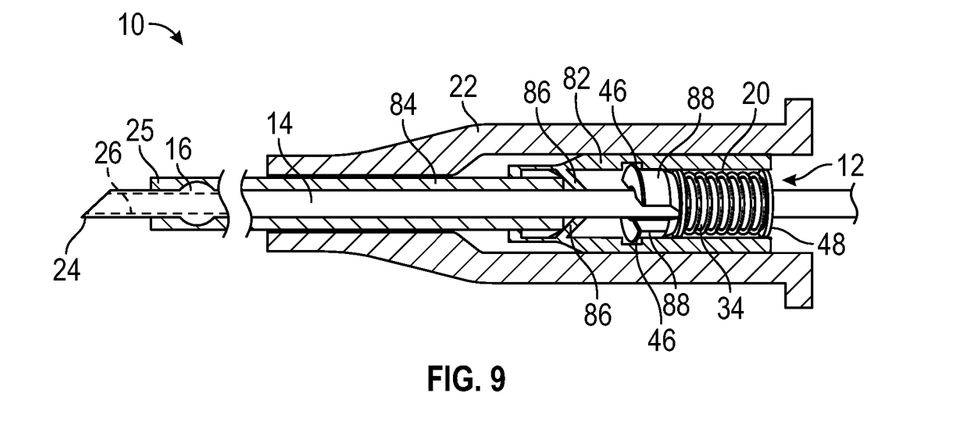
FIG. 9 illustrates a partial cut-away view of a representative embodiment of the cannula capture mechanism of FIG. 1 in which the cannula is exposed from the inner housing, and the cannula capture mechanism is secured to a septum.

Referring now to FIG. 9, in some embodiments, a septum 82 may be configured to move distally over a fixed septum activator 84 to open one or more barriers 86 of the septum 82 and allow the needle 14 to pass through the septum 82, as illustrated in FIG. 9. In some embodiments, and the outer surface of the inner housing 18 may interact with one or more interlock surfaces 88 formed in the inner surface of the septum 82 in a same or similar manner as the interlock surfaces 54 or the interlock surfaces 70 described previously. For example, contraction of the inner housing 18 radially inward, in response to retraction of the needle 14 proximally within the inner housing 18, may cause the one or more interlock components 46 to be separated from the one or more interlock surfaces 88, which may allow removal of the cannula capture mechanism 12 from the septum 82 and the catheter adapter 22, the distal tip 24 of the needle 14 being shielded inside inner housing 18.

The described cannula capture mechanism 12 and associated methods may offer several advantages over certain prior art needle shielding devices. For example, the cannula capture mechanism 12 may be compact and/or may be internal to the catheter device 10. Also, the cannula capture mechanism 12 may provide needle point protection as well as needle point blood containment. Additionally, the cannula capture mechanism 12 may provide a positive, tactile feedback to a clinician, indicating the needle 14 is in the shielded position. Further, the cannula capture mechanism 12 also provides a versatile interlock interface for interfacing with one or more components of a catheter device 10, including, for example, the catheter adapter 22, blood control or port valves, the septum activator 68, etc.

Figure 10A:
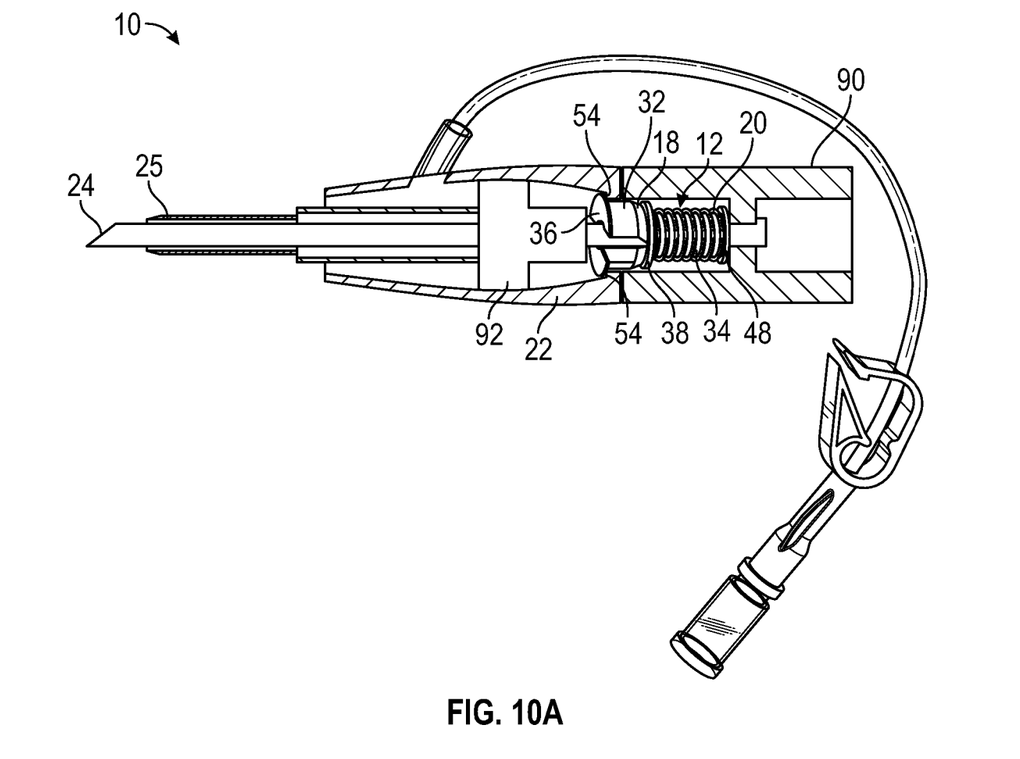
FIG. 10A illustrates a partial cut-away view of a representative embodiment of the cannula capture mechanism of FIG. 1 disposed in an integrated catheter.
Figure 10B:
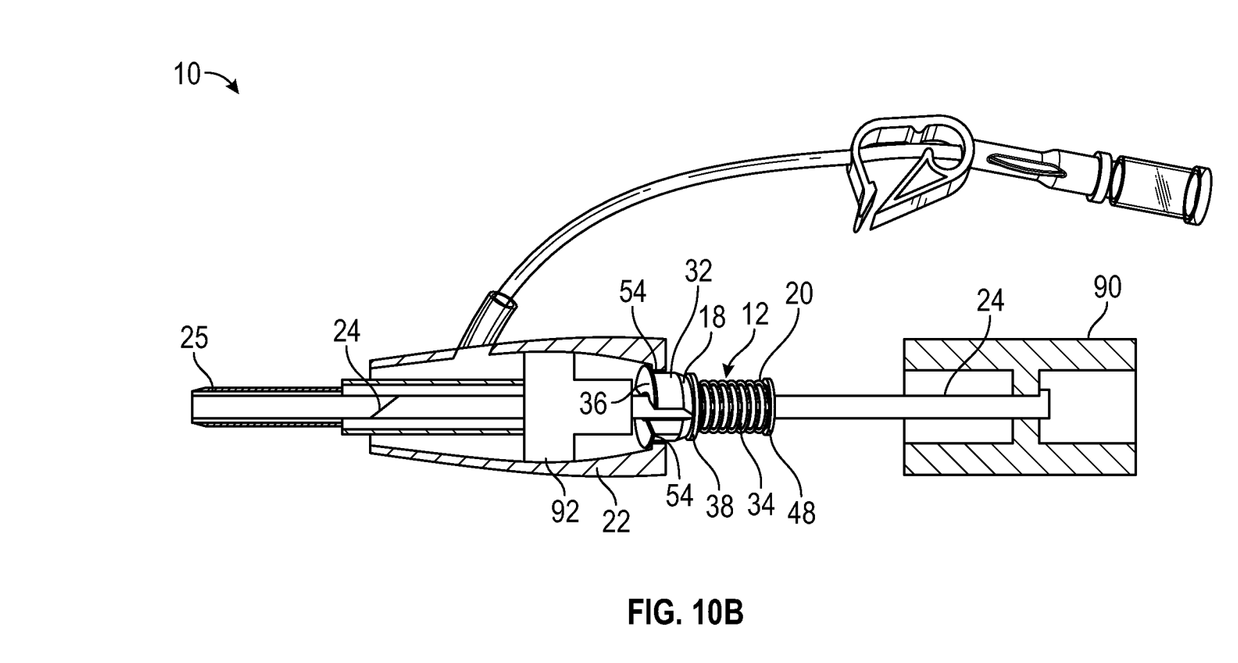
FIG. 10B illustrates a partial cut-away view of a representative embodiment of the cannula capture mechanism of FIG. 1 disposed in the integrated catheter, the cannula being partially retracted.

The cannula capture mechanism 12 may be compatible with a variety of catheter devices, including, for example, ported, straight, and integrated catheter devices, as well as ported and straight blood control catheter devices. Referring now to FIGS. 10A-10B, in some embodiments, when the catheter device 10 includes an integrated catheter, the interlock surfaces 54 may be disposed distal to a needle hub 90 and/or proximal to a septum 92 of the catheter adapter 22. In these and other embodiments, at least a portion of the cannula capture mechanism 12 may be disposed between the septum 92 and the needle hub 90. In some embodiments, the interlock surfaces 54 may be disposed on the septum 92, a septum canister or housing (not illustrated), or on the catheter adapter 22. In some embodiments, a proximal end of the needle 14 may be fixed within the needle hub 90 using any suitable means, including, for example, a feature disposed on the proximal end of the needle 14 and/or an adhesive disposed within the needle hub 90.

The needle hub 90 may include any shape or size. In some embodiments, the needle hub 90 may have an outer diameter approximately equal to or larger than an outer diameter of the catheter adapter 22, which may facilitate use of the needle hub 90 as an insertion grip when moving the needle 14 through the catheter hub 90. In some embodiments, the needle hub 90 may extend distally to partially or fully cover the cannula capture mechanism 12 when the needle 14 is exposed from a distal end of the catheter 25, as illustrated in FIG. 10A.

The present invention may be embodied in other specific forms without departing from its structures, methods, or other essential characteristics as broadly described herein and claimed hereinafter. In some embodiments, particular interlock surfaces, such as the interlock surface 54, may be disposed on a surface of any suitable component of a catheter device, including, for example: a catheter adapter, a septum activator, a blood control septum, an integrated catheter septum, or a septum housing. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A catheter device, comprising:
    an interlock surface;
    a catheter adapter;
    a cannula capture mechanism comprising:
        an outer housing;
        an inner housing comprising an interlock component, wherein at least a portion of the inner housing is disposed within the outer housing, wherein the inner housing comprises a plurality of arms; and
        a cannula that extends into the inner housing, wherein the cannula comprises a distal tip,
        wherein in response to the cannula being retracted proximally with respect to the inner housing and the catheter adapter such that the distal tip is disposed proximal to a distal end of the inner housing, the plurality of arms are configured to move inwardly towards each other, wherein in response to the plurality of arms moving inwardly towards each other, the interlock component is configured to separate from the interlock surface and the outer housing is configured to decompress in a distal direction from a compressed state to a decompressed state to bias the plurality of arms of the inner housing together to prevent the cannula from exiting the distal end of the inner housing.

2. The catheter device of claim 1, wherein when the cannula is exposed from the distal end of the inner housing, the plurality of arms of the inner housing are splayed radially outward and the outer housing is in the compressed state.

3. The catheter device of claim 1, wherein an inner diameter of the distal end of the outer housing is approximately equal to an outer diameter of a distal portion of the inner housing when the plurality of arms are biased together.

4. The catheter device of claim 1, wherein the plurality of arms extend distally from a proximal end of the inner housing.

5. The catheter device of claim 1, wherein the cannula comprises a cannula feature, wherein when the cannula is retracted proximally within the inner housing, the cannula feature is configured to contact a proximal end of the inner housing to prevent the cannula from exiting the proximal end of the inner housing.

6. The catheter device of claim 1, wherein the outer housing comprises a spring portion, wherein the spring portion is compressible along a longitudinal axis aligned with the cannula.

7. The catheter device of claim 1, wherein an inner surface of the catheter adapter or a surface of a component contained within the catheter adapter comprises the interlock surface, wherein interlock surface and the interlock component interact secure the inner housing within the catheter adapter when the cannula is exposed from the distal end of the inner housing.

8. The catheter device of claim 7, wherein the inner surface of the catheter adapter is configured to separate from the inner housing to release the inner housing from the catheter adapter when the cannula is retracted proximally within the inner housing.

9. The catheter device of claim 1, further comprising a septum activator, wherein the septum activator is disposed within an inner lumen of the catheter adapter, wherein an inner surface of the septum activator is configured to secure the inner housing within the catheter adapter when the cannula is exposed from the distal end of the inner housing.

10. The catheter device of claim 9, wherein the inner surface of the septum activator is configured to separate from the inner housing to release the inner housing from the septum activator when the cannula is retracted proximally within the inner housing.

11. A catheter device, comprising:
    a catheter adapter; and
    a cannula capture mechanism, comprising:
        an outer housing;
        an inner housing, wherein at least a portion of the inner housing is disposed within the outer housing; and
        a cannula that extends into the inner housing, wherein when the cannula is exposed from a distal end of the inner housing, a distal portion of the inner housing has a first diameter, wherein when the cannula is retracted proximally within the inner housing, the distal portion of the inner housing has a second diameter and a distal end of the outer housing is configured to decompress in a distal direction and slide distally over the distal portion of the inner housing within the catheter adapter to seal the distal end of the inner housing, wherein the first diameter is greater than the second diameter.

12. The catheter device of claim 11, wherein when the cannula is retracted proximally within the inner housing, the outer housing is configured to decompress.

13. The catheter device of claim 11, wherein the inner housing comprises a plurality of arms, wherein when the cannula is exposed from the distal end of the inner housing, the cannula is configured to bias the plurality of arms apart.

14. The catheter device of claim 13, wherein the distal portion of the inner housing comprises at least a portion of the plurality of arms.

15. The catheter device of claim 13, wherein the plurality of arms extend distally from a proximal end of the inner housing.

16. The catheter device of claim 11, wherein the cannula comprises a cannula feature, wherein when the cannula is retracted proximally within the inner housing, the cannula feature is configured to contact a proximal end of the inner housing to prevent the cannula from exiting the proximal end of the inner housing.

17. The catheter device of claim 11, further comprising a catheter adapter, wherein an inner surface of the catheter adapter is configured to secure the inner housing within the catheter adapter when the cannula is exposed from the distal end of the inner housing and to separate from the inner housing to release the inner housing from the catheter adapter when the cannula is retracted proximally within the inner housing.

18. The catheter device of claim 11, further comprising a septum activator, wherein the septum activator is disposed within an inner lumen of the catheter adapter, wherein an inner surface of the septum activator or septum is configured to separate from the inner housing from the septum activator when the cannula is retracted proximally within the inner housing.

19. A catheter device, comprising:
a cannula capture mechanism comprising:
an outer housing configured to decompress in a distal direction between a compressed and a decompressed state;
an inner housing, wherein the inner housing includes a plurality of interlock components, wherein the plurality of interlock components are disposed on the outer surface of the inner housing such that an outer diameter of the inner housing is increased at the plurality of interlock components; and
a cannula that extends into the inner housing, wherein when the cannula is exposed from a distal end of the inner housing, the plurality of interlock components interact with a plurality of interlock surfaces formed in another surface of the catheter device, wherein when the cannula is retracted proximally within the inner housing, the inner housing contracts radially inward causing the plurality of interlock components to be separated from the plurality of interlock surfaces and the outer housing to move to the decompressed state and extend distally over a distal portion of the inner housing to prevent the cannula from exiting the distal end of the inner housing.

* * * * *